US00PP30040P3

(12) United States Plant Patent
Denardi et al.

(10) Patent No.: US PP30,040 P3
(45) Date of Patent: Jan. 1, 2019

(54) APPLE TREE NAMED 'VENICE'

(50) Latin Name: ***Malus domestica* Borkh**
Varietal Denomination: Venice

(71) Applicant: Empresa de Pesquisa Agropecuária e Extensão Rural de Santa Catarina S.A. (Epagri), Florianópolis, Santa Catarina (BR)

(72) Inventors: Frederico Denardi, Caçador (BR); Marcus Vinicius Kvitschal, Caçador (BR); Maraisa Crestani Hawerroth, Caçador (BR)

(73) Assignee: Empresa de Pesquisa Agropecuária e Extensão Rural de Santa Catarína (Epagri), Santa Catarina (BR)

( * ) Notice: Subject to any disclaimer, the term of this patent is extended or adjusted under 35 U.S.C. 154(b) by 0 days.

(21) Appl. No.: 14/999,707

(22) Filed: Jun. 15, 2016

(65) Prior Publication Data

US 2017/0367231 P1 Dec. 21, 2017

(51) Int. Cl.
*A01H 5/08* (2018.01)
*A01H 6/74* (2018.01)

(52) U.S. Cl.
USPC ..... Plt./161
CPC ..... *A01H 6/7418* (2018.05); *A01H 5/08* (2013.01)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

'Venice' apple tree (*Malus domestica* Borkh) is a new variety selected for its low chilling requirement, resistance to Gala leaf spot disease and partial horizontal resistance to apple scab, high fruit quality, and excellent storageability.

4 Drawing Sheets

Latin name: *Malus domestica* Borkh.
Variety denomination: 'Venice'.

BACKGROUND OF THE VARIETY

'Venice' is a new and distinct variety of apple tree (*Malus domestica* Borkh) obtained from a controlled cross of 'Imperatriz' (female parent, not patented) x 'Baronesa' (male parent, not patented) carried out at Caçador, Santa Catarina, Brazil in 2000. Seeds obtained from the cross were planted at Caçador, and 'Venice' was selected from the resulting seedlings for propagation and further observation. 'Venice' was first asexually propagated by grafting in 2004 at Caçador, and has since been observed to remain true to type over successive asexually propagated generations.

BRIEF DESCRIPTION OF THE VARIETY

'Venice ' apple tree is distinguished by its resistance to Gala leaf spot disease (*Colletotrichum* spp.) and partial horizontal resistance to apple scab (*Venturia inaequalis*), and its low chilling requirement. Fruit of 'Venice' is notable for its high quality, having crisp juicy flesh and a high sugar content, and its excellent storageability.

'Venice' is distinguished from female parent 'Imperatriz' by its smaller, more acidic fruit; later ripening; more intense skin color; and improved storageability.

'Venice' is distinguished from male parent 'Baronesa' by its earlier fruit maturity (10 to 15 days earlier than 'Baronesa'); more coarse flesh texture; higher acidity; and more pronounced overcolor.

'Venice' is distinguished from standard 'Fuji', a similar variety, by its lower chilling requirement which is particularly suited to growing conditions in Brazil; partial horizontal resistance to apple scab; lower tendency to biannual bearing; production of fruit predominantly on spur buds, as compared to 'Fuji', which produces fruit primarily on terminal buds of long shoots; more complete and intense overcolor on fruit; more coarse fruit texture; improved storageability; and increased susceptibility to penicilium fruit rot (*Penicilium espancium*) during storage.

BRIEF DESCRIPTION OF THE PHOTOGRAPHS

The accompanying photographs of the 'Venice' variety were taken from 2013 to 2015 at Caçador, Brazil.

DETAILED BOTANICAL DESCRIPTION OF THE VARIETY

Figure 1:
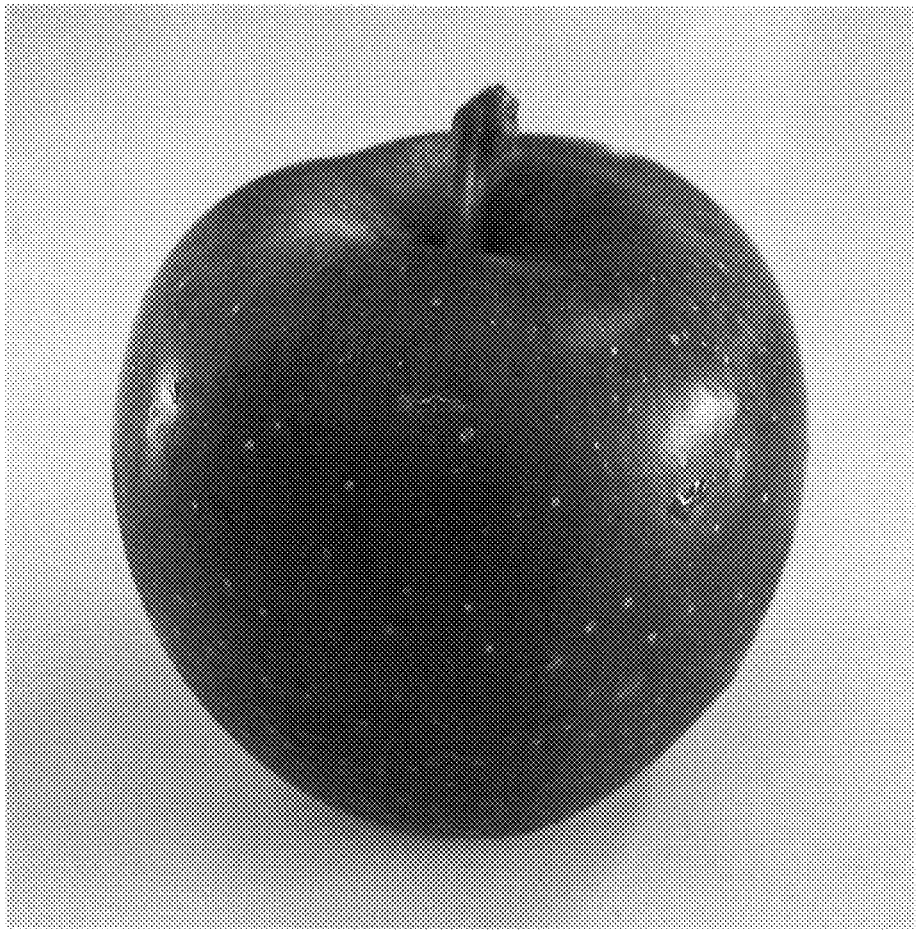
FIG. 1 is a photograph of a 'Venice' apple.
Figure 2:
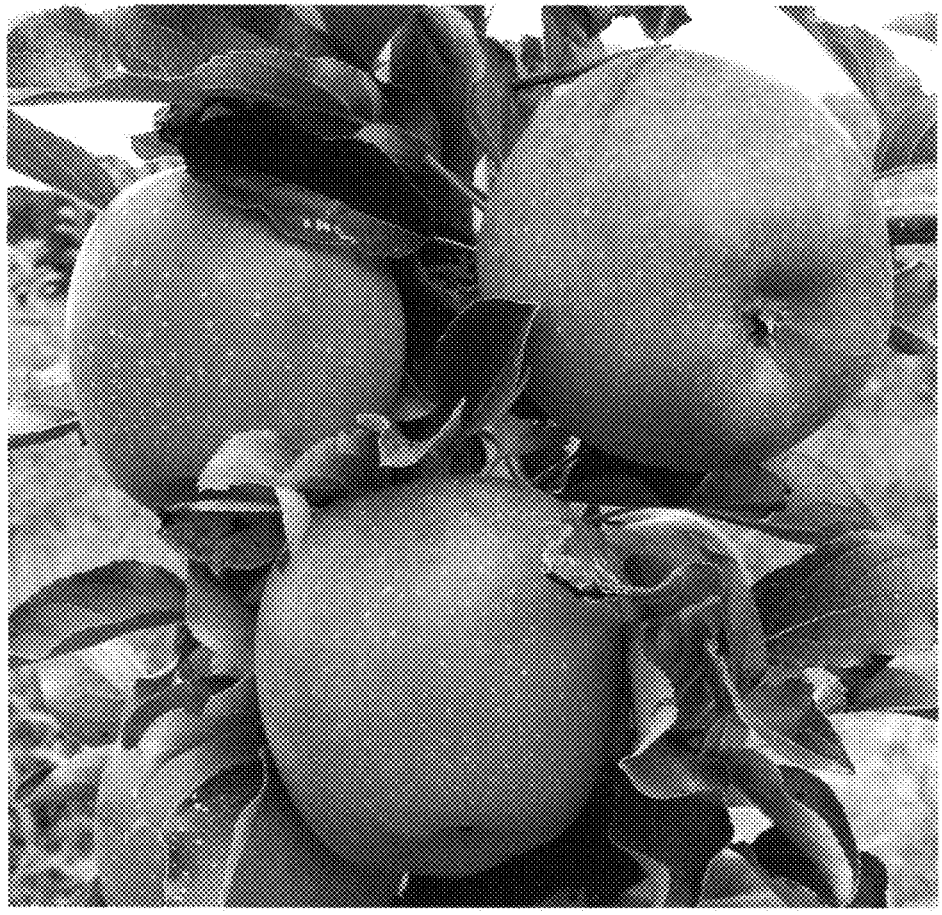
FIG. 2 is a photograph of 'Venice' apples on the tree.
Figure 3:
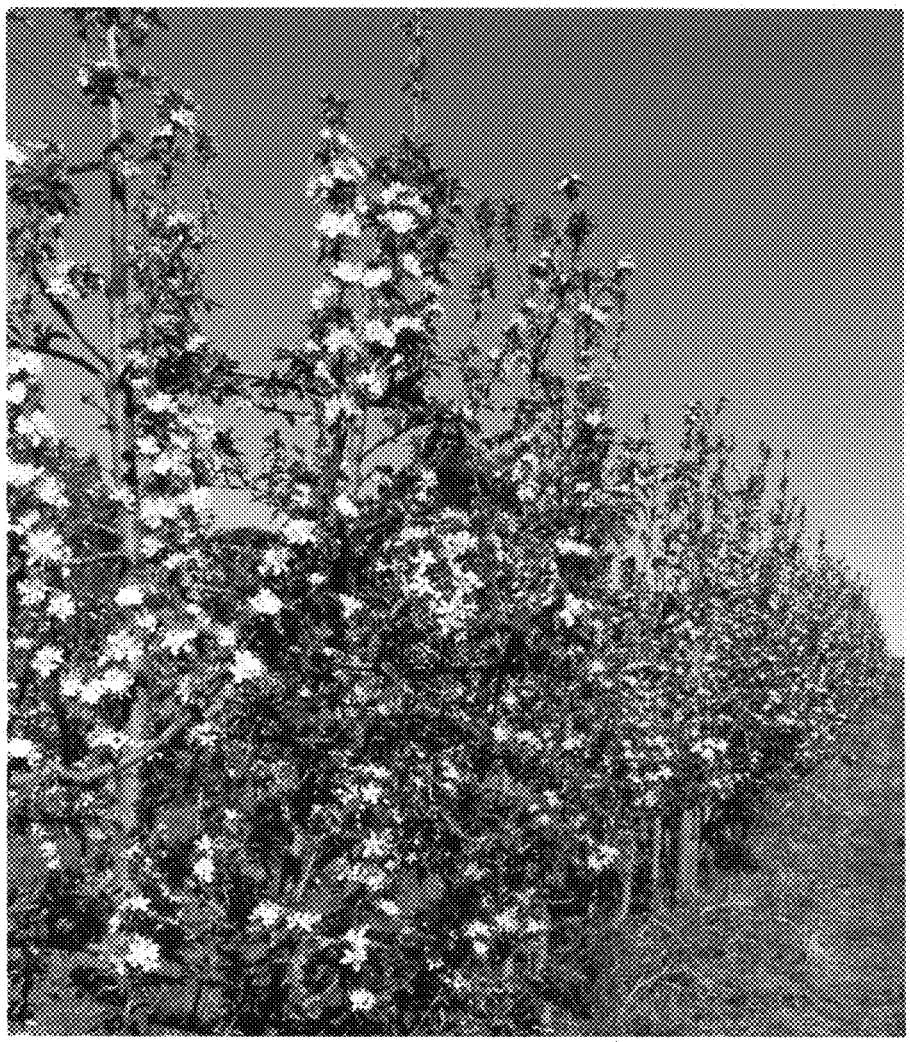
FIG. 3 is a photograph of 'Venice' apple trees in bloom.
Figure 4:
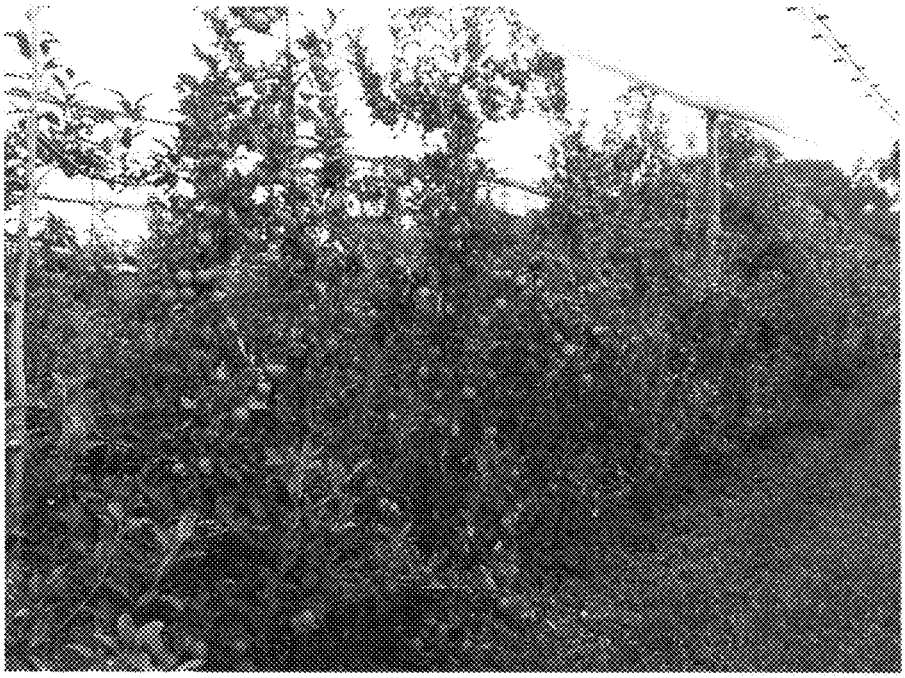
FIG. 4 is a photograph of 'Venice' apple trees and fruit.

The following detailed botanical description is based on observations made at Caçador, Brazil from 2013 to 2015, of trees planted in 2011, grown on 'Marubakaido' rootstock (not patented) with 'M-9' interstock (not patented). All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
*Vigor*.—Medium.
*Type*.—Ramified.
*Habit*.—Spreading.
*Height*.—3.6 m.
*Trunk diameter* (*at* 30 *cm above the graft*).—8.1 cm.
*Bark texture*.—Slightly rough.
*Bark color*.—Yellow-green 148C.
*Lenticel diameter*.—1.6 mm.
*Lenticel shape*.—Round.
*Lenticel color*.—Greyed-yellow 161A.

Branch (fruiting branches located at around 1 m above the graft union):
*Length*.—1.1 m.
*Diameter*.—26 mm.
*Crotch angle*.—80° to 85°.
*Bark color*.—Greyed-green 198A.
*Lenticel diameter*.—1 mm.
*Lenticel shape*.—Round.
*Lenticel color*.—Yellow-white 158A.
*Number of lenticels per cm*2.—3.2.

One year old shoot:
*Length*.—0.7 m.
*Color*.—Greyed-purple 187A.
*Pubescence*.—Weak.
*Thickness*.—6 mm.
*Internode length*.—25 mm.
*Lenticel shape*.—Ovate in transversal direction.
*Lenticel length*.—1.4 mm.
*Lenticel width*.—0.8 mm.
*Lenticel height*.—0.5 mm.
*Lenticel color*.—Greyed-orange 168D.
*Number of lenticels per cm*2.—1.77.

Flower buds:
*Quantity per spur*.—1.33.
*Shape*.—Spiky.
*Length*.—8 mm.
*Diameter*.—4 mm.
*Color*.—Greyed-purple 183A.

Flowers:
*Date of first bloom*.—September 10 to September 18.
*Date of full bloom*.—September 25 to October 3.
*Pollination requirement*.—Yes.
*Diameter of fully open flower*.—40.3 mm.
*Relative position of petal margin*.—Intermediate.
*Number per cluster*.—5.0.
*Flower height*.—13.7 mm.
*Flower fragrance*.—Medium.

Petals:
*Number per flower*.—5.
*Shape*.—Ovate.
*Length*.—19.1 mm.
*Width*.—12.3 mm.
*Apex shape*.—Rounded.
*Base shape*.—Rounded.
*Margin*.—Smooth.
*Color of upper surface*.—Red-purple 69D with purple N78C on apex margin.
*Color of lower surface*.—Purple 77B.

Sepals:
*Quantity*.—5 sepals per flower.
*Sepal color*.—Upper surface — Yellow-green 145B with dark purple brown 59A apex.
*Sepal color*.—Lower surface — Yellow-green 145B with dark purple brown 59A apex.
*Sepal shape*.—Lanceolate.
*Sepal width*.—3.7 mm.
*Sepal length*.—10.1 mm.
*Sepal apex shape*.—Pointed.
*Margin*.—Smooth and pubescent.

Pistils:
*Length*.—11.2 mm.
*Quantity*.—5.
*Color*.—Green-white 157A.

Anthers:
*Quantity*.—18.7.
*Anther length*.—1.9 mm.
*Anther width*.—1.3 mm.
*Anther color*.—Yellow 8B.
*Presence of pollen*.—Yes.
*Pollen quantity*.—Abundant.
*Color of pollen*.—Yellow 8B.

Stigma:
*Length*.—0.6 mm.
*Color*.—Yellow-green N144D.

Style:
*Length*.—6.5 mm.
*Color*.—Yellow-green — N144D.

Ovary:
*Size*.—3.2 mm (width)×3.9 mm (length).
*Color*.—Greyed-green 194C.

Leaves:
*Shape*.—Ovate.
*Length*.—10 cm.
*Width*.—5 cm.
*Length/width ratio*.—2.
*Blade margin*.—Crenate.
*Apex shape*.—Acute.
*Base shape*.—Rounded.
*Color of upper surface*.—Green N137A.
*Color of lower surface*.—Yellow-green 146D.
*Leaf texture*.—Upper surface — Smooth.
*Leaf texture*.—Lower surface — Slightly velvety.
*Leaf venation pattern*.—Cross-venulate.
*Leaf vein color*.—Upper surface — Yellow-green 145B.
*Leaf vein color*.—Lower surface — Yellow-green 145C.
*Attitude in relation to shoot*.—Upward.

Petiole:
*Length*.—33 mm.
*Diameter*.—2 mm.
*Color*.—Yellow-green 148A.

Fruit:
*Fruit per cluster*.—3 to 5.
*Diameter*.—70 mm.
*Height*.—64 mm.
*Weight*.—173 g.
*Ratio of height to width*.—1.09.
*General shape in profile*.—Conical.
*Position of maximum diameter*.—On the third near to the stalk cavity.
*Ribbing*.—Narrow.
*Crowning at calyx end*.—Weak.
*Diameter of eye*.—6 mm.
*Length of sepal*.—7 mm.
*Bloom of skin*.—Absent to weak.
*Greasiness of skin*.—Absent to weak.
*Background color of skin*.—Green-yellow 1C.
*Over color of skin*.—Orange-red N34A.

*Amount of over color.*—70% to 90%.
*Intensity of over color*.—Medium.
*Pattern of over color*.—Solid flush with weakly defined stripes.
*Amount of russet around stalk cavity*.—Medium.
*Amount of russet on cheeks*.—Absent.
*Area of russet around eye basin*.—Absent.
*Length of stalk.*—19 mm.
*Thickness of stalk.*—3 mm.
*Depth of stalk cavity.*—8 mm.
*Width of stalk cavity.*—26 mm.
*Stalk color*.—Greyed-brown N199D.
*Depth of eye basin.*—11 mm.
*Width of eye basin.*—20 mm.
*Fruit locule quantity.*—5.
*Fruit locule length.*—20.2 mm.
*Fruit locule width.*—2.6 mm.
*Firmness of flesh.*—18 to 18.5 pounds.
*Flesh texture*.—Fine.
*Aroma*.—Medium.
*Juiciness*.—High.
*Brix.*—14° to 14.5° Brix.
*Flesh color*.—Yellow 4D.

Seeds:
*Quantity per fruit.*—7.8.
*Seed length.*—8.8 mm.
*Seed width.*—2.7 mm.
*Shape*.—Ovate.
*Color*.—Greyed-orange 166A.

Harvest:
*Harvest date* (*actual and relative*).—Mid-season (second half of March in Brazil).
*Number of picks*.—Two.
*Amount of fruit produced per tree per harvest.*—20 to 25 kg per tree.

Disease resistance/susceptibility: Susceptible, but with some horizontal resistance to apple scab (*Venturia inaequalis*) — not immune; Resistant to Gala leaf spot (*Colletotrichum* spp.); tolerance to powdery mildew (*Podosphaera leucotricha*); Susceptible to penicilium fruit rots in storage (*Penicilium espancium*).

Winter hardiness: Hardy in region tested (USDA hardiness zone 11b); Low chilling requirement suitable for climate in region tested.

Market use: Fresh.

We claim:

1. A new and distinct apple tree as described and illustrated herein.

* * * * *